США010163361B2

United States Patent
Chen et al.

(10) Patent No.: US 10,163,361 B2
(45) Date of Patent: Dec. 25, 2018

(54) BEHAVIOR SHAPING USING A CONSTRUCTION TOY

(71) Applicant: FUJITSU LIMITED, Kawasaki-shi, Kanagawa (JP)

(72) Inventors: Cong Chen, Cupertino, CA (US); Ajay Chander, San Francisco, CA (US); Kanji Uchino, Santa Clara, CA (US)

(73) Assignee: FUJITSU LIMITED, Kawasaki (JP)

( * ) Notice: Subject to any disclaimer, the term of this patent is extended or adjusted under 35 U.S.C. 154(b) by 232 days.

(21) Appl. No.: 15/076,602

(22) Filed: Mar. 21, 2016

(65) Prior Publication Data

US 2017/0270815 A1 Sep. 21, 2017

(51) Int. Cl.
*G09B 19/00* (2006.01)
*A63H 33/04* (2006.01)
(Continued)

(52) U.S. Cl.
CPC ............. *G09B 19/00* (2013.01); *A61B 5/16* (2013.01); *A61B 5/165* (2013.01); *A61B 5/168* (2013.01); *A61B 5/7267* (2013.01); *A63H 33/04* (2013.01); *A63H 33/042* (2013.01); *A63H 33/046* (2013.01); *G06N 99/005* (2013.01);
(Continued)

(58) Field of Classification Search
None
See application file for complete search history.

(56) References Cited

U.S. PATENT DOCUMENTS 6,157,872 A * 12/2000 Michael ............... A63H 33/042
700/247
2003/0040250 A1* 2/2003 Yim ....................... A63H 33/04
446/91
(Continued)

FOREIGN PATENT DOCUMENTS

KR 2010-0107998 A 10/2010
WO 2013/052644 A1 4/2013

OTHER PUBLICATIONS

Wolfe, Katie et al. "Promoting Behavioral Variability in Individuals With Autism Spectrum Disorders a Literature Review." Focus on Autism and Other Developmental Disabilities vol. 29, No. 3, Mar. 24, 2014, pp. 180-190.
(Continued)

*Primary Examiner* — Jason Yen
(74) *Attorney, Agent, or Firm* — Maschoff Brennan

(57) ABSTRACT

A method includes acquiring individual assessment data that includes behavior from player of a construction toy. The construction toy includes at least one sensor to detect an activity of the player with the construction toy. The method further includes determining a goal for the player based on the individual assessment data and a set of group assessment data. The method also includes providing a teaching based on the goal. The method includes permitting the player to play with the construction toy with reduced monitoring or intervention by the processing device during a free play period. The method further includes in response to a determination that free play period is over, prompting the player to perform an activity based on the goal. The method also includes in response to a determination that the player has completed the activity, providing a first reinforcement message to the player.

20 Claims, 12 Drawing Sheets

(51) Int. Cl.
*G09B 5/06* (2006.01)
*A61B 5/16* (2006.01)
*A61B 5/00* (2006.01)
*G06N 99/00* (2010.01)
*G09B 5/00* (2006.01)
*A63F 3/04* (2006.01)

(52) U.S. Cl.
CPC ............... *G09B 5/00* (2013.01); *G09B 5/06* (2013.01); *A63F 2003/0489* (2013.01); *A63F 2250/26* (2013.01); *A63H 2200/00* (2013.01)

(56) References Cited

U.S. PATENT DOCUMENTS

| | | | | |
|---|---|---|---|---|
| 2010/0093425 | A1* | 4/2010 | Tsuchiya | G07F 17/32 463/20 |
| 2010/0248830 | A1* | 9/2010 | Otomo | A63F 13/10 463/31 |
| 2012/0258436 | A1* | 10/2012 | Lee | G09B 19/00 434/362 |
| 2015/0269813 | A1* | 9/2015 | Severance | G06Q 40/04 463/9 |
| 2015/0282752 | A1 | 10/2015 | Roots et al. | |

OTHER PUBLICATIONS

GravitySketch2015, Retrieved on Mar. 19, 2016. Retrieved from <https://www.gravitysketch.com/index.html>.

Elison, Jed T., et al. "Repetitive behavior in 12-month-olds later classified with autism spectrum disorder." Journal of the American Academy of Child & Adolescent Psychiatry vol. 53, Issue 11, Nov. 1, 2014: 1216-1224.

Zuckerman, K., et al "Parental Concerns, Provider Response, and Timeliness of Autism Spectrum Disorder Diagnosis." The Journal of pediatrics, vol. 166, Issue 6, Jun. 2015, pp. 1431-1439.e1.

Albinali, F., et al, "Recognizing stereotypical motor movements in the laboratory and classroom: a case study with children on the autism spectrum." Proceedings of the 11th international conference on Ubiquitous computing. ACM, Sep. 30, 2009.

Goncalves, N., et al. "Preliminary study on determining stereotypical motor movements." Engineering in Medicine and Biology Society (EMBC), 2012 Annual International Conference of the IEEE. IEEE, Aug. 28, 2012.

Riesen, Kaspar, and Horst Bunke. "Approximate graph edit distance computation by means of bipartite graph matching." Image and Vision Computing vol. 27, Issue 7, Jun. 4, 2009, pp. 950-959.

Nikolic, Mladen. "Measuring similarity of graph nodes by neighbor matching." Intelligent Data Analysis, vol. 16, Issue 6, Sep. 27, 2012, pp. 865-878.

Karypis, G., et al., "Chameleon: Hierarchical clustering using dynamic modeling." Computer vol. 32, Issue 8 (Aug. 1999): 68-75.

Runco, Mark A., and Garrett J. Jaeger. "The standard definition of creativity." Creativity Research Journal vol. 24, Issue 1, Feb. 10, 2012, pp. 92-96.

Hassink, S., "AAP Statement on U.S. Preventive Services Task Force Draft Recommendation Statement on Autism Screening" American Academy of Pediatrics, Aug. 3, 2015. Retrieved from <https://www.aap.org/en-us/about-the-aap/aap-press-room/Pages/AAP-Statement-on-U-S-Preventive-Services-Task-Force-Draft-Recommendation-Statement-on-Autism-Screening.aspx>.

Stiles, Joan, and Catherine Stern. "Developmental change in spatial cognitive processing: Complexity effects and block construction performance in preschool children." Journal of Cognition & Development. May 2001, vol. 2 Issue 2, p. 157-187. 31, p. 1.

Hosoi, T., et al. "A-blocks: recognizing and assessing child building processes during play with toy blocks." SIGGRAPH Asia 2014 Emerging Technologies. ACM, Nov. 2014.

Kleinman, Jamie M. et al. "Diagnostic Stability in Very Young Children with Autism Spectrum Disorders." Journal of autism and developmental disorders vol. 38, Issue 4, Apr. 2008, pp. 606-615. PMC. Web. Mar. 18, 2016.

"Prevalence of Autism Spectrum Disorder Among Children Aged 8 Years—Autism and Developmental Disabilities Monitoring Network, 11 Sites, United States, 2010." Autism and Developmental Disabilities Monitoring Network Surveillance Year 2010 Principal Investigators. (2014). Centers for Disease Control and Prevention Morbidity and Mortality Weekly Report. Mar. 28, 2014, vol. 63, No. 2, pp. 1-21.

European Search Report for corresponding application No. EP 16 20 5542, dated Jul. 26, 2017.

* cited by examiner

1100

1105

| 2-year-old | Dimensionality | Stage | Size | Symmetry |
|---|---|---|---|---|
| 5% | 0 | N/A | 1 | N/A |
| 10% | 1 | Tower | 3 | 1 |
| 25% | 1 | Line | 3 | 1 |
| 50% | 2 | Cross | 4 | 0.45 |
| 75% | 2 | Enclosure | 8 | 0.6 |
| 95% | 2 | Bridge | 8 | 0.75 |

1110

BEHAVIOR SHAPING USING A CONSTRUCTION TOY

FIELD

The embodiments discussed in the present disclosure are related to behavior shaping using a construction toy.

BACKGROUND

Construction toys have been available in relatively the same state for a number of years. Example construction toys may include Legos® and Lincoln Logs®. Construction toys may be used for enjoyment as well as for learning and teaching.

The subject matter claimed in the present disclosure is not limited to embodiments that solve any disadvantages or that operate only in environments such as those described above. Rather, this background is only provided to illustrate one example technology area where some embodiments described may be practiced. Furthermore, unless otherwise indicated, the materials described in the background section are not prior art to the claims in the present application and are not admitted to be prior art by inclusion in this section.

SUMMARY

According to an aspect of an embodiment, a method includes acquiring individual assessment data that comprises behavior of a player of a construction toy. The construction toy includes at least one sensor to detect an activity of the player with the construction toy. The method further includes determining a goal for the player based on the individual assessment data and a set of group assessment data. The method also includes providing a teaching based on the goal. The method includes permitting the player to play with the construction toy with reduced monitoring by the processing device during a free play period. The method further includes prompting the player to perform an activity based on the goal in response to a determination that free play period is over. The method also includes providing a first reinforcement message to the player in response to a determination that the player has completed the activity.

The object and advantages of the implementations will be realized and achieved at least by the elements, features, and combinations particularly pointed out in the claims.

It is to be understood that both the foregoing general description and the following detailed description are given as examples and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
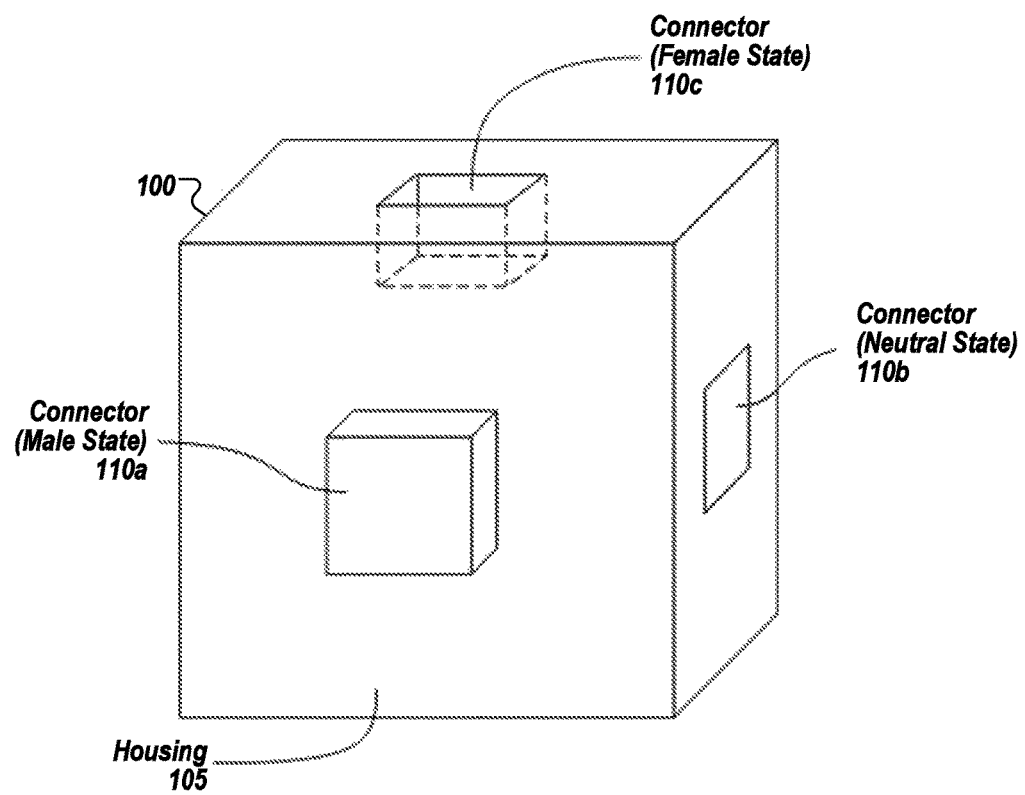
FIG. 1 illustrates an example construction toy with one or more controllable connectors.

Early detection of various disorders and diseases, such as autism, may be difficult. For example, an average diagnosis age for autism is around 4 years old in United States [Kleinman, Jamie M. et al. "Diagnostic Stability in Very Young Children with Autism Spectrum Disorders." *Journal of autism and developmental disorders* 38.4 (2008): 606-615. *PMC Web.* 18 Mar. 2016], while a child may be diagnosed as young as 2 years [Autism and Developmental Disabilities Monitoring Network Surveillance Year 2010 Principal Investigators. (2014). Prevalence of Autism Spectrum Disorder Among Children Aged 8 Years—Autism and Developmental Disabilities Monitoring Network, 11 Sites, United States, 2010." *Centers for Disease Control and Prevention Morbidity and Mortality Weekly Report.* 63(2), 1-21]. This gap between the detectable age and average diagnosis age may be due to a relative difficulty for humans to notice early signs of autism. System and methods of detecting and modeling behavior is further described in U.S. patent application Ser. No. 15/075,125, filed Mar. 19, 2016, which is incorporated herein by reference.

Aspects of the present disclosure pertain to shaping behavior using a construction toy. In at least one embodiment, the construction toy may be suitable for use by a small child. With an added interest in the construction toy, the small child may be more likely to play with the construction toy more frequently. The systems and methods described herein, including the construction toy, may be used to guide the child's behavior with little or no human interaction. More frequent play by the child may result in growth and learning by the child.

The present disclosure also related to technology that serves as a play coach to shape a person's behavior toward higher variability, flexibility, and complexity. A system may automate various steps of Applied Behavior Analysis for improving behavior variability. The steps may include: automatic data collection and assessment during play, intervention planning, and intervention tools (e.g., new skill teaching, prompting, scheduling, reinforcement).

Systems and methods may include an apparatus (e.g., a game or toy), an instrument embedded in the apparatus, and a coaching computer program. The apparatus may include a computer game, or a digitally enhanced toy controllable by a computer program. The instrument may include a hardware component with sensors to measure the location, orientation, acceleration, etc. of the apparatus. The instrument may also include a software module of a computer game collecting players' behavior data in the game. The coaching program may include a software module that reads the measurements from the instrument and gives interaction instructions (e.g., generating output). The coaching program may run on a separate computing device connected to the apparatus or right on the apparatus.

Systems and method described herein may be used as assessment and intervention tool for developmental disorders and cognitive disorders (e.g., autism and intellectual disability). Other embodiments may include educational games and toys (e.g., piano toy, chess-like games). Other embodiments may be directed to other types of behavior coaching, such as stress measurement using a sensor-enabled computer keyboard.

FIG. 1 illustrates an example construction toy 100 with one or more controllable connectors. The one or more controllable connectors may be adjustable between at least two connectivity states so as to allow, encourage, discourage or prevent connection of the construction toy 100 to an adjacent construction toy. In at least one embodiment, the connectivity states include male, female, and neutral states. In at least one alternative embodiment, the connectivity states may include enabled and disabled states.

The construction toy 100 may include a housing 105 of any shape or size. The housing 105 may include any number of sides or walls. The housing 105 may include a solid piece of material and may also include one or more cavities for various components, such as a sensor, operating assembly, etc., as described below. As illustrated, the housing 105 includes a cube with six external walls to form six sides. The housing 105 may include any number of sides.

The construction toy 100 may also include one or more controllable connectors 110. As illustrated, the construction toy 100 includes three connectors—a male state connector 110a, a neutral state connector 110b, and a female state connector 110c. As illustrated, the connectors 110a, 110b, 110c may include a shape with a square profile. The connectors 110a, 110b, 110c may be any shape or size. The construction toy 100 may include any number of connectors 110 and any number of connectors 110 may be positioned on a particular side on the construction toy 100.

The housing 105 may also include one or more cavities or voids through which the one or more connectors 110 may be coupled. As illustrated, the cavities in the housing are substantially the same shape as the connectors 110 with the square profile. The male state connector 110a may extend through a first cavity and outward with respect to the housing 105. The male state connector 110a may be configured to fit within a female state connector of an adjacent construction toy (not illustrated). The female state connector 110c may be recessed in a second cavity with respect to an outer surface of the housing of the adjacent construction toy. The neutral state connector 110b may be substantially parallel with an outer surface of the housing 105 such that the neutral state connector 110b may be flush with the outer surface of the housing 105.

The construction toy 100 may be part of a set of construction toys that may be connected to and decoupled from each other. Each construction toy in the set be associated with store a block identifier. Similarly, each connector on each construction toy in the set may be associated with a connector identifier. In at least one embodiment, the connector identifier may be associated with a respective construction toy. For example, a construction toy may include a block identifier "ABC123" and a first connector of the construction toy may include a first connector identifier "ABC123:001", a second connector of the construction toy may include a second connector identifier "ABC123:002", a third connector of the construction toy may include a third connector identifier "ABC123:003", and so on. The connector identifiers may also be associated with a block map that identifies the location of each of the connector with respect to each other. For example, a cube-shaped construction toy 100 may have six connectors with one connector on each face. The block map may include the six faces as locations for the six connectors. The block identifiers may be integrated into the block map, such that the first connector identifier "ABC123:001" is indicative of the first connector being on a first of the six faces, the second connector identifier "ABC123:002" being indicative of the second connector being on a second of the six faces, and so on. In at least one alternative embodiment, the location of the connector with respect to the construction toy 100 is separate from the block identifier and the connector identifier. The block identifier, the block map, and the connector identifier may be stored on another device, such as on another construction toy or a host computer device.

Each construction toy in the set may include at least one location sensor capable of reading its location relative to adjacent construction toys that are near or connected to the construction toy. The location sensor may also be capable of reading a location of an adjacent construction toy relative to the construction toy. Each construction toy in the set may selectively control its respective connectors in response to predefined rules and its location relative to adjacent blocks that are near or connected to the construction toy. For example, each construction toy in the set may selectively control its respective connectors to retract a connector to prevent repetitive behavior, to guide a player to build the construction toys in a new directions, or to detect and manage repetitive patterns, as further described below.

Figure 2:
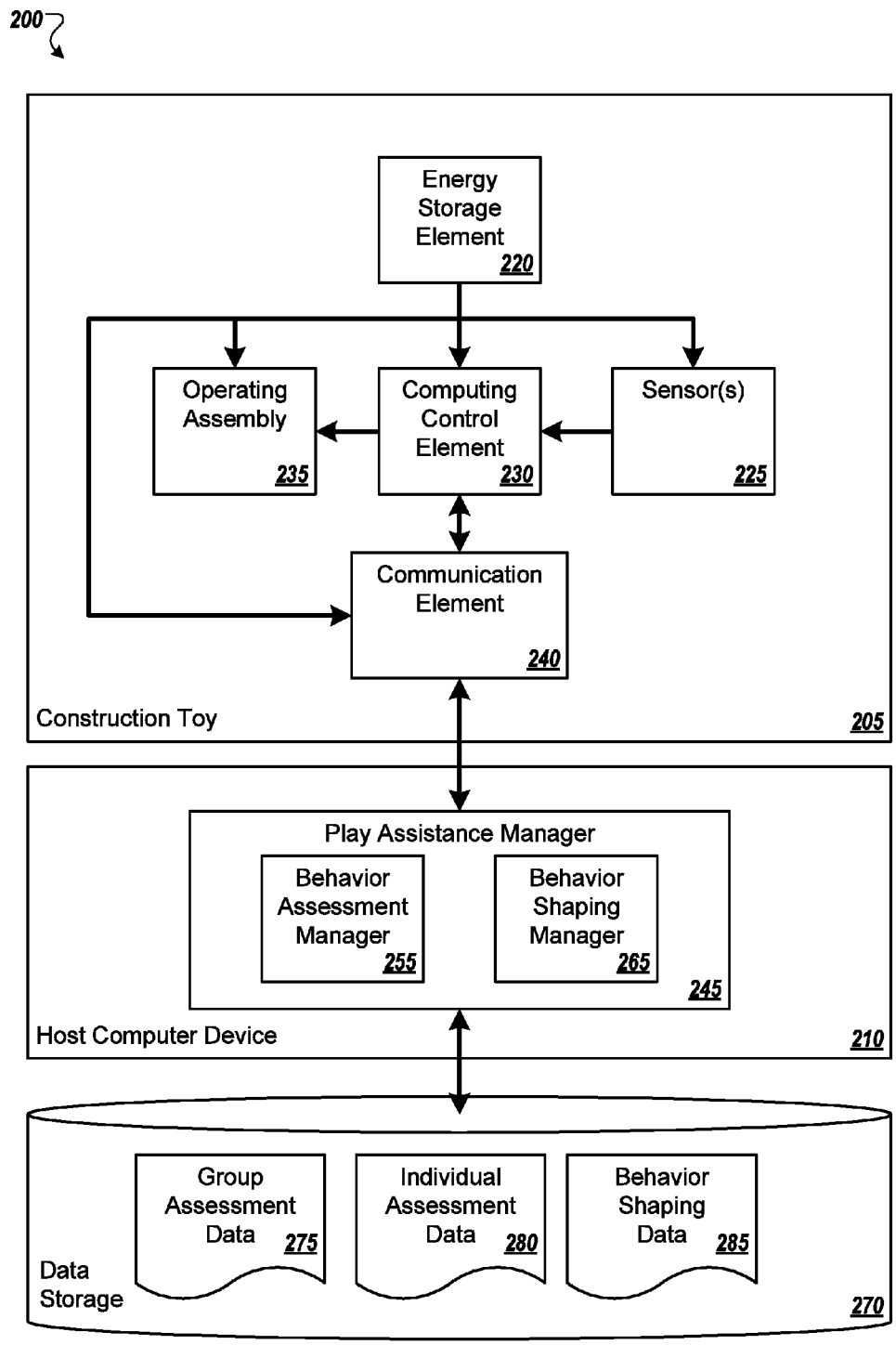
FIG. 2 illustrates a block diagram of an example operating environment in which some embodiments may be implemented.

FIG. 2 illustrates a block diagram of an example operating environment in which some embodiments may be implemented. The operating environment 200 may include a construction toy 205 and a host computer device 210. The construction toy 205 may be the same as or similar to the construction toy 100 of FIG. 1. The host computer device 210 may monitor construction of a set of construction toys and may determine transformations to be performed on connectors of the construction toys. The construction toy 205 may detect and send location data to the host computer device 210 and execute received commands. The construction toy 205 may include an energy storage element 220, one or more sensors 225, a computing control element 230, an operating assembly 235, and a communication element 240.

The construction toy 205 may be part of a set of construction toys that may be coupled to and decoupled from each other. Each construction toy in the set may include at least one sensor 225 capable of reading its location relative to adjacent blocks that are near or connected to the construction toy. The at least one sensor 225 may also be capable of reading a location of an adjacent construction toy relative to the construction toy 205. Each construction toy may also include a programmable computing control element to execute computer programs and to operate the connectors.

The energy storage element 220 may supply electrical power to the one or more sensors 225 computing control element 230, operating assembly 235, and communication element 240. The energy storage element 220 may include a charging device and/or an energy conversion component that may transform power in real time. The energy storage element 220 may include a battery or other similar device configured to store energy.

The one or more sensors 225 may be configured to detect a characteristic of an adjacent construction toy. The characteristic of the adjacent construction toy may include proximity, location, motion, position, orientation, temperature, emitted or reflected light, radio frequency identification (RFID), etc. The one or more sensors 225 may include a proximity sensor, NFC sensor, sonar sensor, infrared sensor, temperature sensor, light sensor, motion sensor, accelerometer, gyroscope, orientation sensor, etc. to detect the characteristic of the adjacent construction toy. The one or more sensors 225 may be operatively connected to the computing control element 230 and the one or more sensors 225 may send data to the computing control element 230. For example, a sensor 225 may detect that the construction toy 100 has been operatively coupled to an adjacent construction toy. The sensor 225 may send data indicative of the coupling—including a block identifier of the construction toy 205, a connector identifier of the construction toy 205 that was coupled to the adjacent construction toy, a block identifier of the adjacent construction toy, a connector identifier of the adjacent construction toy, etc. Alternatively, each construction toy may gather and report data for itself and not for other construction toys. For example, the sensor 225 may send data indicative of the coupling—including a block identifier of the construction toy 205, a connector identifier of the construction toy 205 that was coupled to the adjacent construction toy, etc. The adjacent construction toy may send a respective a block identifier of the adjacent construction toy, a connector identifier of the adjacent construction toy, etc. The sensor data may be sent to the computer control element 230, to the communication element 240 and/or to the host computer device 210. Using these and other techniques, data pertaining to the coupling of construction toys may be collected and sent to the host computer device 210.

The computing control element 230 may include a processor to execute instructions and operate the operating assembly 235. The computing control element 230 may include processing logic to control the operating assembly 235 to change state of one or more connectors. The computing control element 230 may include a programmable computer element. The computing control element 230 may receive instructions from the host computer device 210 pertaining to the control of the one or more connectors. The instructions may relate to changing a state of one or more connectors to encourage or discourage certain behavior of the player of the construction toy 205, as further described below.

The operating assembly 235 may include a connector and a mechanism to change the state of the connector. An example operating assembly 235 may include an actuator and a shaft coupled to the connector to actuate the connector to different connectivity states, as further described in conjunction with FIGS. 3, 4A, 4B and 4C. Another example operating assembly 235 may include a magnetic or electromagnetic connector that may be selectively powered to change the connectivity state of the connector, as further described in conjunction with FIGS. 5 and 6.

The communication element 240 may be attached to the computing control element 230 to communicate with a paired host computer device 210. The communication element 240 may connect to any other device, such as the host computer device 210, using any form of wireless communication capability. In some embodiments, the communication element 240 may include a radio frequency (RF) antenna. By way of example and not limitation, the communication element 240 may be configured to provide, via wireless mechanisms, LAN connectivity, Bluetooth connectivity, Wi-Fi connectivity, NFC connectivity, M2M connectivity, D2D connectivity, GSM connectivity, 3G connectivity, 4G connectivity, LTE connectivity, any other suitable communication capability, or any suitable combination thereof. The construction toy 205 may include any number of communication elements 240. The construction toy 205 may connect to any network, such as wide area networks (WANs) and/or local area networks (LANs). For example, secured and/or encrypted data may be exchanged between the construction toy 205 and the host computer device 210. In some embodiments, the network includes the Internet, including a global internetwork formed by logical and physical connections between multiple WANs and/or LANs. Alternately or additionally, the network may include one or more cellular RF networks and/or one or more wired and/or wireless networks such as, but not limited to, 802.xx networks, Bluetooth access points, wireless access points, IP-based networks, meshed devices, or the like. The network may also include one or more servers that enable one type of network to interface with another type of network.

The host computer device 210 may include one or more client or server computing devices, (such as a personal computer (PC), game console, set top box, laptop, mobile phone, smart phone, tablet computer, netbook computer, e-reader, personal digital assistant (PDA), or cellular phone, wearable device, electronic wristwatch, arm band, chest strap, head band, bracelet, wristband, rackmount server, a router computer, a server computer, a personal computer, a mainframe computer, a laptop computer, a web server, a proxy server, a desktop computer, etc.), data stores (e.g., hard disks, memories, databases), networks, software components, and/or hardware components. The host computer device 210 may include a play assistance manager 245.

The play assistance manager 245 may model and guide behavior of a player of a set of construction toys. The play assistance manager 245 may generate instructions to control various the connectivity state of connectors in the set of construction toys, including the construction toy 205. The play assistance manager 245 may receive data from the one or more sensors 225 via the communication element 240. The play assistance manager 245 may use the received data to determine when to change a state of one or more connectors. The play assistance manager 245 may include a set of predetermined rules that indicate when to change a state of one or more connectors. The predetermined rules may include one or more conditions for a change of state of a connector. When the play assistance manager 245 determines (based on sensor data) that a player is engaging in repetitive behavior when playing with the construction toys, for example, the play assistance manager 245 may generate an instruction to change the connectivity state of one or more connectors to encourage different the player to engage in different techniques to play with the construction toys. In some embodiments, the play assistance manager 245 may include a stand-alone application ("app") that may be downloadable either directly from a host or from an application store. The play assistance manager 245 may include a behavior assessment manager 255 and a behavior shaping manager 265.

The behavior assessment manager 255 may determine various characteristics pertaining to a player of a set of construction toys. The behavior assessment manager 255 may monitor and model the construction made by the set of construction toys. The behavior assessment manager 255 may monitor how the player interacts with the set of construction toys and may record every connection the player may make between construction toys. The behavior assessment manager 255 may group structurally similar constructions. The behavior assessment manager 255 may also measure behavior variability and complexity between the constructions. For example, as a player builds a house, the behavior assessment manager 255 uses sensor data from the one or more sensors 225 to determine the player's progress on building the house. The behavior assessment manager 255 may also generate a visualization of the measured behavior variability and complexity between the constructions over time. The behavior assessment manager 255 may also generate a visualization for a particular object the player is building. For example, as the player connects construction toys, the behavior assessment manager 255 may update the digital representation of the house to reflect the physical progress of the house. The behavior assessment manager 255 may also generate a chart or graph to visualize the player's activities over time.

The behavior shaping manager 265 may generate and/or manage a construction model that may include a set of instructions for building a particular object. The construction model may also include a set of guided instructions to encourage learning and/or a particular behavior. The construction model may also include a digital (e.g., graphical) representation of a current configuration of the set of construction toys. For example, when the player builds a house out of the set of construction toys, the construction model may be a digital representation of the house. The construction model may also guide the player on how to build a particular object. The construction model may include the current configuration of the set of construction toys and one or more locations for where to place the next construction toy to build the particular object. A helper may observe the digital representation of the set of construction toys and may define an instruction to be sent to the construction toy 205. The helper may include any individual or computer that may provide assistance to the player. For example, when the helper identifies a particular undesired behavior of the player, the helper may define an instruction to discourage or prevent the particular undesired behavior of the player. The instruction may include an instruction to disable connections between some or all of the construction toys.

The behavior shaping manager 265 may generate and provide guidance to a player of the set of construction toys. The behavior shaping manager 265 may generate instructions to control various the connectivity state of connectors in a set of construction toys, including the construction toy 205. The behavior shaping manager 265 may receive data from the one or more sensors 225 via the communication element 240. The play assistance manager 245 may use the received data to determine when to change a state of one or more connectors. The play assistance manager 245 may include a set of predetermined rules that indicate when to change a state of one or more connectors. The predetermined rules may include one or more conditions for a change of state of a connector. When the behavior shaping manager 265 determines (based on sensor data) that a player is engaging in repetitive behavior when playing with the construction toys, for example, the behavior shaping manager 265 may generate an instruction to change the connectivity state of one or more connectors to encourage different the player to engage in different techniques to play with the construction toys.

Moreover, the behavior shaping manager 265 may, for example, identify a particular behavior of the player and determine whether to coach the player to modify the particular behavior. The behavior shaping manager 265 may provide various outputs to shape the player to modify the particular behavior. In at least one embodiment, the behavior shaping manager 265 may use data generated by the play assistance manager 245 to identify and shape a behavior. For example, the behavior shaping manager 265 may compare the group assessment data 275 with the individual assessment data 280 to identify how close the player's behavior is to her peers' behavior. When the behavior shaping manager 265 determines that the player's behavior is different than her peers' behavior based on such a comparison, the behavior shaping manager 265 may use the behavior shaping data 285 to determine teaching, prompting and/or reinforcement to guide the player, as further described below.

In at least one embodiment, the construction toy 205 and the host computer device 210 are integrated into a single digital platform. In this embodiment, the construction toy 205 may be a digitized or digital representation of the construction toy 205. The player may interact with the digitized construction toy 205 via an application. For example, the application may include a construction toy building game and an interface (e.g., a graphical user interface (GUI) by which the player may interact with construction toys. Some or all of the components of the host computer device 210 may be part of the application. For example, the application may include at least portions of the behavior assessment manager 255 and a behavior shaping manager 265. The application may permit the player to interact with digitized construction toys while monitoring and guiding the player, all from within the application. In at least one embodiment, the player may interact with the application on a user device, which may be operatively coupled to the host computer device 210, such as via a network. The application may send data to the host computer device 210 via the network. The host computer device 210 may process the data and may send instructions to the application via the network.

Figure 3:
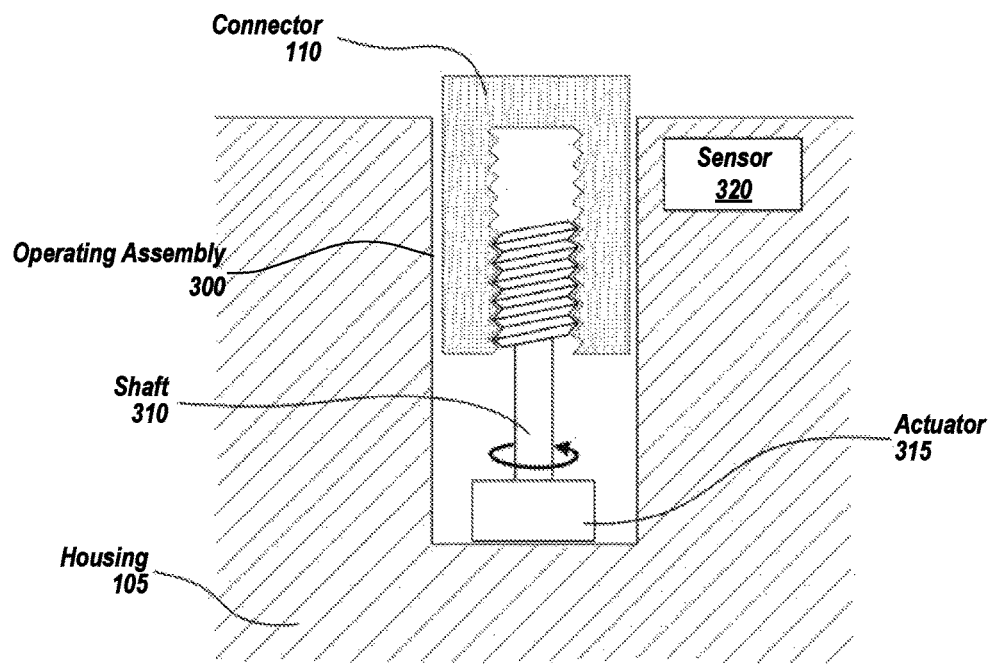
FIG. 3 illustrates an example operating assembly.

FIG. 3 illustrates an example operating assembly 300. The operating assembly 300 may be the same as or similar to the operating assembly 235 described in conjunction with FIG. 2. As illustrated, the operating assembly 300 includes a connector 110, a shaft 310, and an actuator 315. The connector 110 may be coupled to the shaft 310 which may be coupled to the actuator 315 such that movement of the actuator 315 and/or the shaft 310 may cause translational movement of the connector 110 with respect to an outer surface of the housing 105. In at least one embodiment, the actuator 315 may cause rotational movement of the shaft 310. The shaft 310 may be coupled to the actuator on a first end and may have threads on a second end. The connector 110 may include threads that may be coupled to the shaft 310 at the threaded end of the shaft 310. The connector 110 may be rotationally fixed such that rotational movement of the connector 110 may be restricted. In this configuration, rotational movement of the shaft 310 may cause the connector 110 to laterally translate out of and into the housing 105.

The operating assembly 300 may also include a sensor 320 near the connector, which may be used to detect coupling to an adjacent connector. The sensor 320 may be the same as or similar to the sensor 225 of FIG. 2. The sensor 320 may detect a proximity and/or state of a connector on an adjacent construction toy (i.e., an alien connector), the presence of which may be used to transform the connector to a compatible state with the alien connector. For example, if the alien connector is in a female state, the connector on the construction toy may be changed to a male state so as to enable coupling of the construction toy to the adjacent construction toy. In another example, in response to detecting the alien connector or the adjacent construction toy, the connector on the construction toy may be changed to a neutral state to disable coupling of the construction toy to the adjacent construction toy.

Figure 4A:
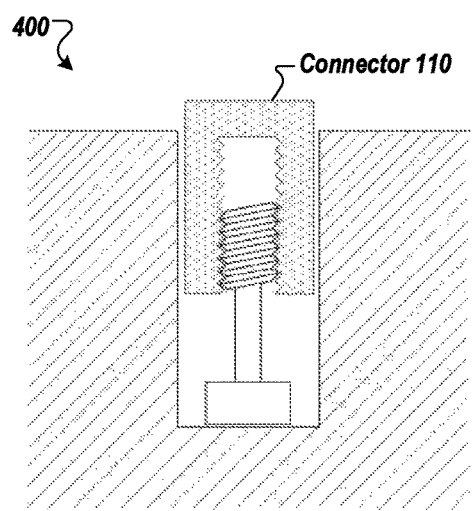
FIGS. 4A, 4B and 4C illustrate three different connectivity states of the operating assembly of FIG. 3.
Figure 4B:
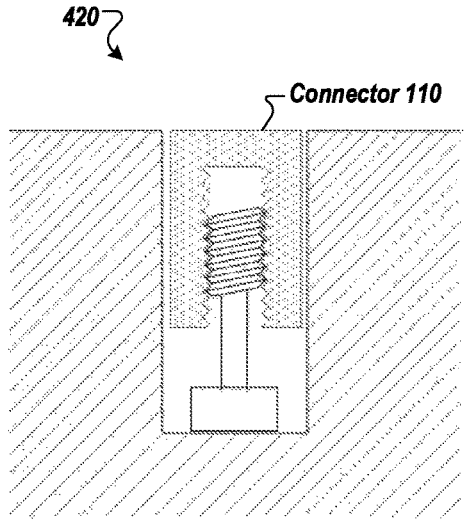
Figure 4C:
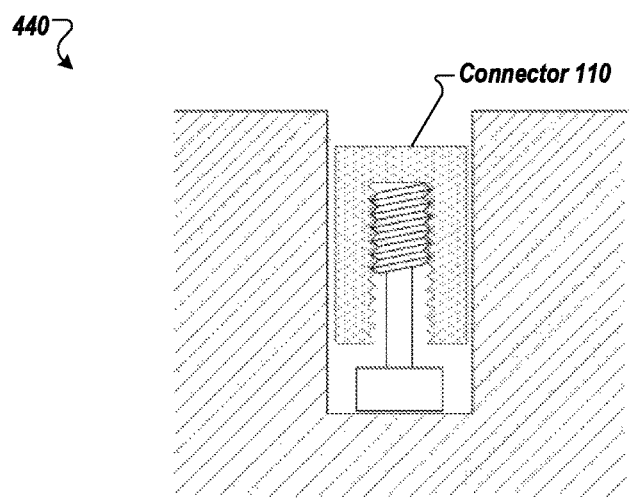

FIGS. 4A, 4B and 4C illustrate three different connectivity states 400, 420, 440 of the operating assembly 300 of FIG. 3. As illustrated in FIG. 4A, the connector 110 is in a male configuration such that the connector 110 extends outward from the housing. As illustrated in FIG. 4B, the connector 110 is in a neutral configuration such that the connector 110 is substantially flush with an outside surface of the housing. As illustrated in FIG. 4C, the connector 110 is in a female configuration such that the connector 110 is recessed within the housing.

Figure 5:
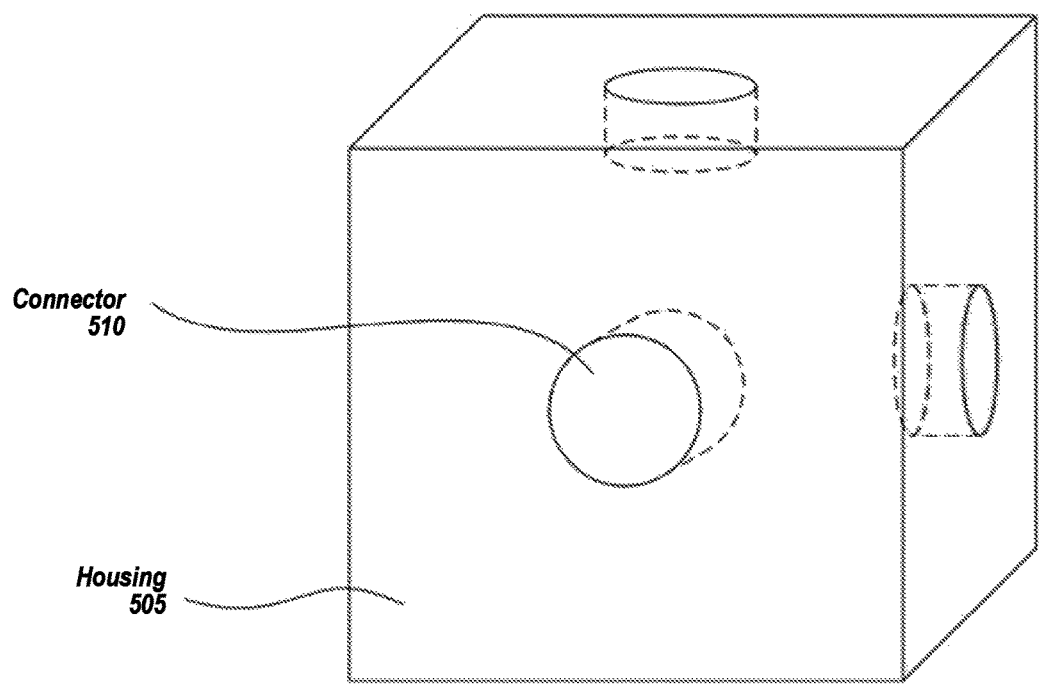
FIG. 5 illustrates another embodiment of a construction toy that includes a housing and at least one electromagnetic connector.

FIG. 5 illustrates another embodiment of a construction toy 500 that includes a housing 505 and at least one electromagnetic connector 510. The housing 505 may be the same as or similar to the housing 105 of FIG. 1. As illustrated, the construction toy 500 includes three electromagnetic connectors. The electromagnetic connectors may be selectively powered on or off to enable or disable coupling to the particular connector. Additionally, the polarity of electromagnetic connectors may be selectively flipped to enable or disable coupling to the particular connector.

Figure 6:
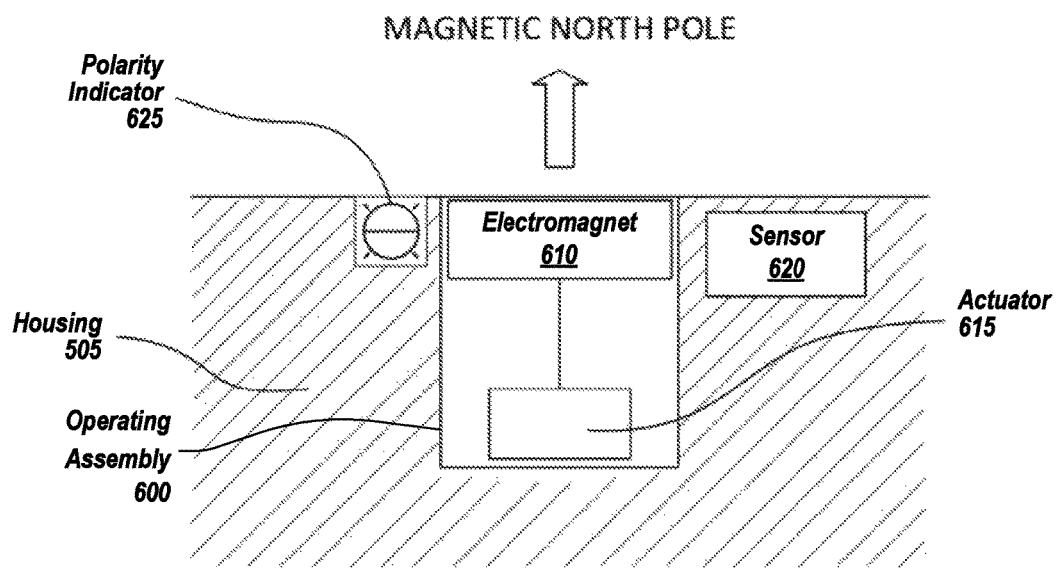
FIG. 6 illustrates another example operating assembly.

FIG. 6 illustrates another example operating assembly 600. The operating assembly 600 may be the same as or similar to the operating assembly 235 described in conjunction with FIG. 2. As illustrated, the operating assembly 600 includes an electromagnetic connector 610 and an actuator 615. The electromagnetic connector 610 may be coupled to the actuator 315 such that movement of the actuator 315 may cause the electromagnetic connector 610 to power on or off. In a powered on state, the electromagnetic connector 610 may be operable to be coupled to an adjacent construction toy. Specifically, the electromagnetic connector 610 may be coupled to an electromagnetic connector of the adjacent construction toy.

The operating assembly 600 may also include a sensor 620 near the electromagnetic connector 610, which may be used to detect coupling to an adjacent electromagnetic connector. The sensor 620 may be the same as or similar to the sensor 225 of FIG. 2. The sensor 620 may detect a proximity and/or state of a connector on an adjacent construction toy (i.e., an alien connector), the presence of which may be used to transform the connector to a compatible state with the alien connector. For example, if the alien connector is in a powered on state, the connector on the construction toy may be changed to a powered on state so as to enable coupling of the construction toy to the adjacent construction toy. In another example, in response to detecting the alien connector or the adjacent construction toy, the connector on the construction toy may be changed to a powered off state to disable coupling of the construction toy to the adjacent construction toy.

The operating assembly 600 may also include a polarity indicator 625. The polarity indicator 625 may indicate a current state of the electromagnetic connector 610 (north or south, positive or negative). The actuator 615 may flip the polarity of electromagnetic connector 610, such as in response to receiving a polarity instruction from a host computer. To flip the polarity of the electromagnetic connector 610, the actuator 615 may alternate a direction of electric current. In at least one embodiment, the polarity indicator 625 includes a light (e.g., LED light) that may be adjacent to the electromagnetic connector 610. In at least one embodiment, the polarity indicator 625 includes a light that is attached to the electromagnetic connector 610. In at least one embodiment, a first state of the polarity is indicated by a first wavelength (or range) or color of light and a second state of the polarity is indicated by a second wavelength (or range) or color of light. In at least one alternative embodiment, a first state of the polarity is indicated by a first blinking pattern of the light and a second state of the polarity is indicated by a second blinking pattern of the light.

Figure 7:
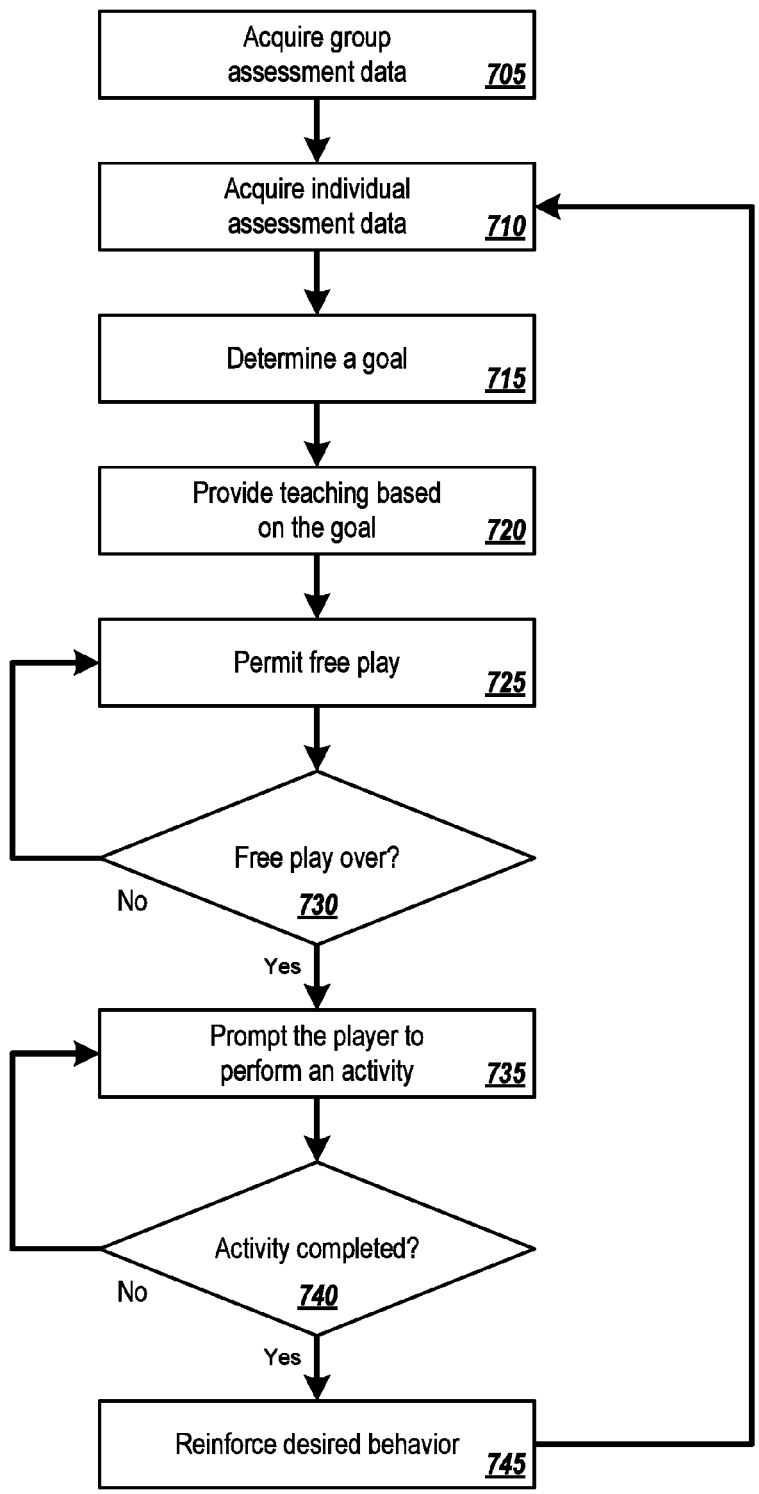
FIG. 7 illustrates a flow diagram of an example method to shape behavior using a set of construction toys.
Figure 8:
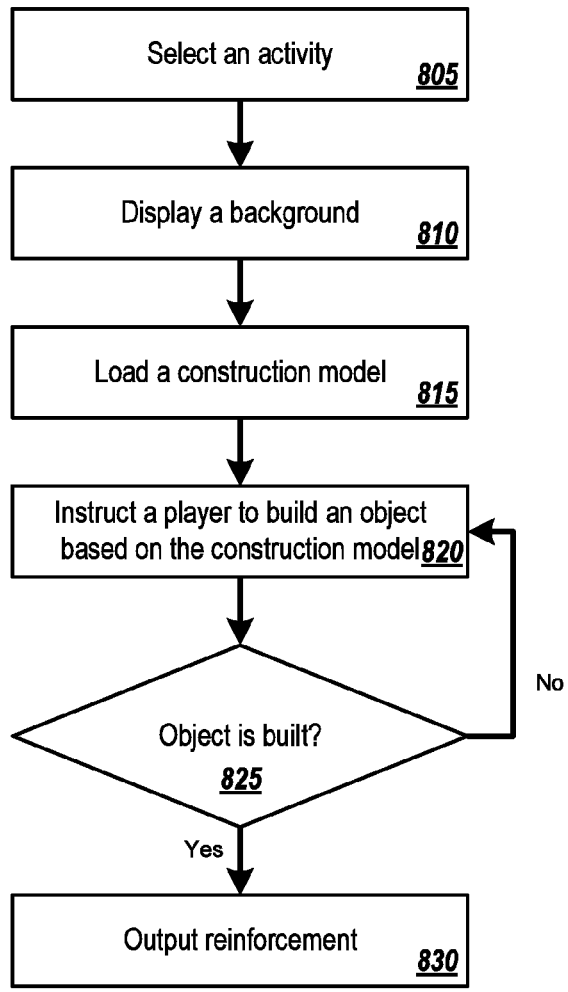
FIG. 8 illustrates a flow diagram of an example method to perform teaching based on a goal.
Figure 9:
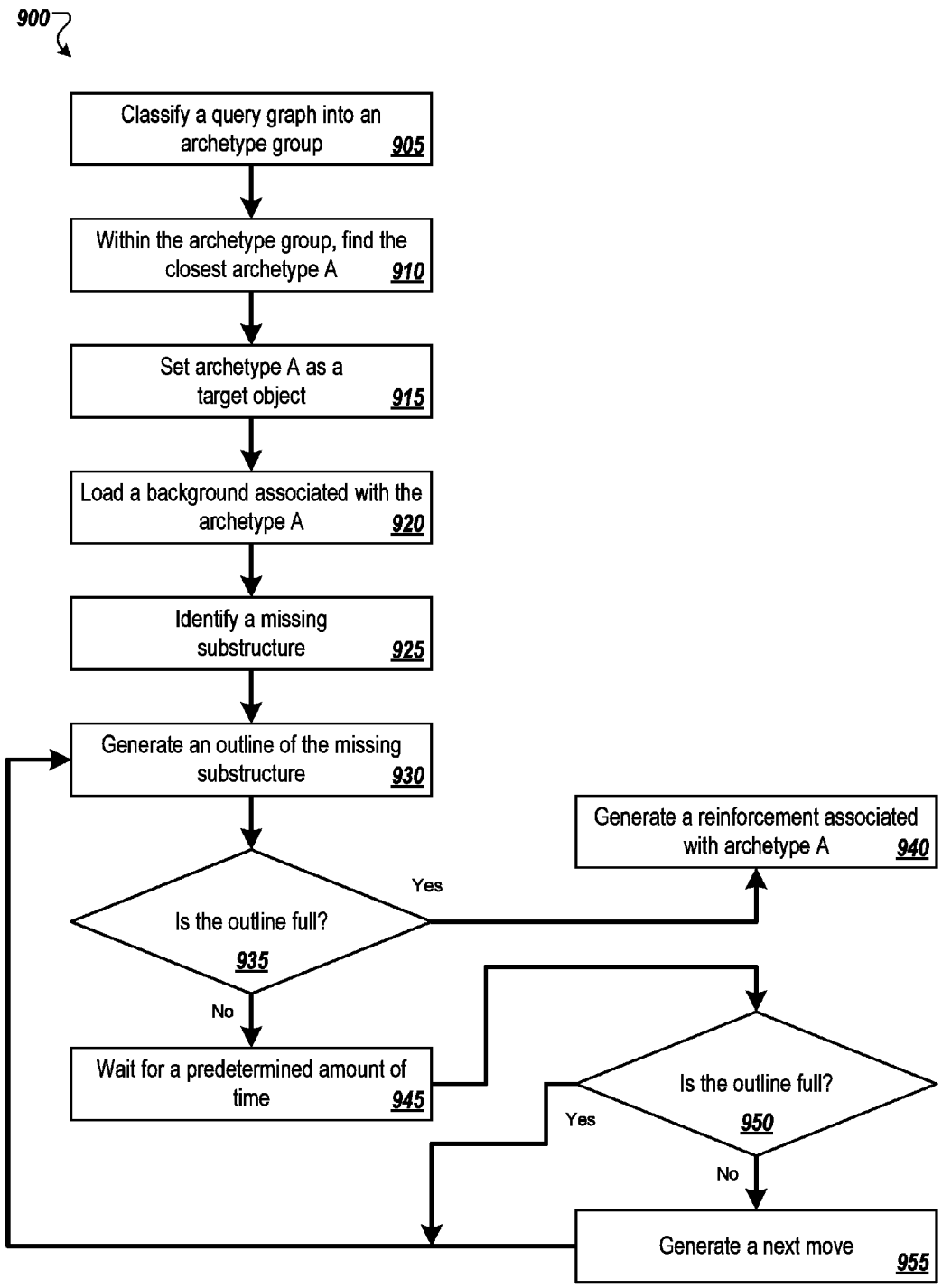
FIG. 9 illustrates a flow diagram of an example method to prompt a player to perform an activity related to a construction toy.

FIGS. 7-9 illustrate flow diagrams of example methods to shape behavior of a player of one or more construction toys that may be implemented, for example, in the operating environment of FIG. 2, arranged in accordance with at least one embodiment described in the present disclosure. The methods may be performed by processing logic that may include hardware (circuitry, dedicated logic, etc.), software (such as is run on a general purpose computer system or a dedicated machine), or a combination of both, which processing logic may be included in the construction toy 205 of FIG. 1. For simplicity of explanation, methods described herein are depicted and described as a series of acts. However, acts in accordance with this disclosure may occur in various orders and/or concurrently, and with other acts not presented and described herein. Further, not all illustrated acts may be required to implement the methods in accordance with the disclosed subject matter. In addition, those skilled in the art will understand and appreciate that the methods may alternatively be represented as a series of interrelated states via a state diagram or events. Additionally, the methods disclosed in this specification are capable of being stored on an article of manufacture, such as a non-transitory computer-readable medium, to facilitate transporting and transferring such methods to computing devices. The term article of manufacture, as used herein, is intended to encompass a computer program accessible from any computer-readable device or storage media. Although illustrated as discrete blocks, various blocks may be divided into additional blocks, combined into fewer blocks, or eliminated, depending on the desired implementation.

FIG. 7 illustrates a flow diagram of an example method 700 to shape behavior using a set of construction toys. The set of construction toys may include one or more of the construction toys described in this document, such as the construction toy 100 of FIG. 1. The method 700 may begin at block 705, where processing logic may acquire group assessment data. The group assessment data may include data received via manual input from a helper or data collected from two or more players while the players interacted with one or more construction toys. The group assessment data may include aggregate data of multiple players. Example group assessment data is described in conjunction with FIGS. 11A and 11B. The processing logic may record every connection the player may make between construction toys. The processing logic may identify structurally similar constructions. In at least one embodiment, the processing logic may identify the structurally similar constructions by analyzing the connections between made by the player between construction toys and identifying similarities within the various constructions. For example, the structurally similar constructions may include various four legged objects (e.g., animals) of various shapes of sizes. The processing logic may identify the four legs as being a common characteristic of each of these structurally similar constructions. The processing logic may group structurally similar constructions. In at least one embodiment, the processing logic may name or categorize each group of structurally similar constructions.

At block 710, the processing logic may acquire individual assessment data. The processing logic may measure behavior variability, behavior novelty, complexity, and build categories between the constructions. For a given time period p, the behavior variability may be measured based on operational variability and structural variability. Behavior novelty may be measured by construction novelty. Construction complexity may be measured by one or more of size, stage complexity, dimensionality complexity, arches complexity, or symmetry. In at least one embodiment, the processing logic may acquire individual assessment data using techniques described in F1423.10286US01, which is incorporated by reference. Example individual assessment data is further described in conjunction with FIG. 10.

At block 715, the processing logic may determine a goal. The goal may include a particular behavior or a particular construction configuration. For example, for a player who performs repetitive activities when playing with the construction toys, the goal may be to encourage the player to perform other, new activities. The player, for example, may have played with the construction toys a number of time, but each time, the player may have built the same or similar object, such as a two-dimensional tower. The goal may include encouraging the player to build something other than a two-dimensional tower. In another example, the goal may include having the player build a specific object, such as a four-sided building. To determine the goal, the processing logic may analyze the individual assessment data and determine what the player may do to continue to learn while playing with the construction toys. For example, the two-dimensional tower may have a first stage rating, which may correspond to a complexity, a skill level, a tiered-learning program, etc. Once the processing logic determines that the player has mastered the tower at the first stage rating, the processing logic may set the goal as encouraging the player to build an object within the second stage rating. In at least one embodiment, the processing logic may determine mastery of a stage rating by identifying a threshold number of objects within the particular stage rating that were built by the player.

At block 720, the processing logic may provide teaching based on the goal. The teaching may include a visual presentation, such as via a user device. In at least one embodiment, the set of construction toys may be part of an electronic video game, where the player may interact with electronic representations of the set of construction toys via the user device. The visual presentation may include, for example, an active region (e.g., a highlighted area, an outline, or a shadow) where the player is to place the next construction toy. For a physical set of construction toys, the processing logic may generate and send an instruction to one or more of the construction toys to enable or disable a connector to facilitate or prevent certain types of behavior consistent with the goal. The processing logic may provide teaching according to the techniques described in conjunction with FIG. 8.

At block 725, the processing logic may permit free play. During the free play, the player may interact with the set of construction toys without (or with reduced) behavior shaping. The processing logic may permit free play for a set duration of time and/or may permit free play based on milestones. For example, the free play may end once the player has completed (or nearly completed) building an object. The processing logic may periodically check whether free play should end. When the free play is not over ("NO" at block 730), the processing logic may proceed to block 725.

When the free play is over ("YES" at block 730), the processing logic may prompt the player to perform an activity at block 735. The activity may be based on the goal and/or based on the teaching from block 720. The activity may include a request to build at least a portion of an object. The prompting may include a visual prompt and/or a connector-based prompt (e.g., enable or disable a connector of one or more construction toys). The prompting may include general or direct prompting. General prompting may include themed-play sessions. For example, the general prompting may include subtle prompts for the player to build buildings, and the general prompting may include a theme related to buildings (e.g., a city skyline, roads with open areas for buildings, etc.). General prompting may also include prompting a next step for the player with a dynamically generated outline to illustrate when the next construction toy may be placed. Direct prompting may include connecting two construction toys for the player (such as within an electronic construction toy game). Further details pertaining to the prompting are described in conjunction with FIG. 9. The processing logic may periodically monitor to determine whether the player has completed the activity. When the player has not completed the activity ("NO" at block 740), the processing logic may proceed to block 735.

When the player has completed the activity ("YES" at block 740), the processing logic may reinforce the desired behavior at block 745. The processing logic may reinforce the desired behavior by providing a prompting or notification to the player. The notification may include a text-based message, an audible message, a reward, a digital token, and the like. In at least one embodiment, the processing logic may follow a schedule when reinforcing the desired behavior. In an example, the processing logic may follow a protocol to determine which instance of a behavior may be reinforced (e.g., after every correct response, or for every 2 correct responses, etc.). In another example, the processing logic may use computerized scheduling, such as a Lag X schedule, such as in [Lee, Ronald, Jennifer J McComas, and Jennifer Jawor. "The Effects of Differential and Lag Reinforcement Schedules on Varied Verbal Responding by Individuals with Autism." *Journal of Applied Behavior Analysis* 35.4 (2002): 391-402. PMC. Web. 21 Mar. 2016.], the entirety of which is incorporated by reference, or a percentile schedule, such as in [Galbicka, Gregory. "Shaping in the 21st Century: Moving Percentile Schedules into Applied Settings." *Journal of Applied Behavior Analysis* 27.4 (1994): 739-760. PMC. Web. 21 Mar. 2016.], the entirety of which is incorporated by reference. Under a Lag X schedule, the processing logic may reinforce a current response if the current response is different than a previous X responses. Under a percentile schedule, the current response may be reinforced if current response is ranked above a given threshold determined by a given reinforcement probability FIG. 8 illustrates a flow diagram of an example method 800 to provide teaching based on a goal. The goal may be similar to the goal described in conjunction with FIG. 7. At block 805, the processing logic may select an activity. The activity may be based on the goal and performance of the activity may help the player to achieve the goal.

At block 810, the processing logic may display a theme background related to the building activity (e.g., a city skyline, roads with open areas for buildings, etc.).

At block 815, the processing logic may load a construction model. Loading the construction model may include sending instructions to the construction toy 205 of FIG. 2, or providing within a electronic application via an interface. The construction model may include step-by-step instructions for how to build an object. The processing logic may select the object from a collection of objects and identify the corresponding construction model. In at least one embodiment, the processing logic may provide a list of the collection of objects to the player and/or the helper. The processing logic may receive a selection of one of the objects from the collection and may identify the corresponding construction model. The processing logic may provide the construction model to a user device. Alternatively, the processing logic may present the construction model via a display.

At block 820, the processing logic may instruct the player to build the object. To instruct the player to build the object, the processing logic may present step-by-step instructions for how to build the object. Alternatively or additionally, the processing logic may manipulate (e.g., enable, disable, etc.) one or more connectors among construction toys to instruct the player.

At block 820, the processing logic may determine whether the object is built. To determine whether the object is built, the processing logic may receive sensor data to determine that two construction toys have been connected to each other. The processing logic may determine, based on the sensor data, that connections made between construction toys correspond to the object. In at least one embodiment when the player may build an electronic representation of the object (such as via an application on a user device), the processing logic may identify that the object has been built by analyzing the electronic representation of the object within the application. When the processing logic determines that object has not been built ("NO" at block 825), the processing logic may proceed to block 820. When the processing logic determines that the object is built ("YES" at block 825), the processing logic may output a reinforcement at block 830.

FIG. 9 illustrates a flow diagram of an example method 900 to prompt a player to perform an activity related to a construction toy. The activity may include, for example, completing a construction of a particular object. At block 905, the processing logic may classify a query graph into an archetype group. The query graph may include an object to be built, including a partially built object or an object that has not yet been started. The archetype group may include a predetermined group of objects that may be structurally similar. The archetype group may be made by clustering similar constructions that were built by multiple players. An example archetype group may include a group of four legged animals. The processing logic may identify one or more structural features of the query graph and, based at least partially on those one or more structural features, the processing logic may identify an archetype group to which the query graph may fit.

At block 910, the processing logic may identify a closest archetype A which is structurally closest to the query graph among the other archetypes in the archetype group. At block 915, the processing logic may set the archetype A as a target object. The target object may refer to the object that the processing logic may encourage the player to build.

At block 920, the processing logic may load a theme background associated with the archetype A (e.g., a city skyline, roads with open areas for buildings, etc.).

At block 925, the processing logic may identify a missing substructure in the query graph. In at least one embodiment, to identify the missing substructure, the processing logic may compare the archetype A and the query graph and determine differences in construction toys. The processing logic may identify any number of missing substructures.

At block 930, the processing logic may generate an outline of the missing substructure (e.g., general prompting). The outline may serve as a guide or instruction for where the player is to place the next construction toy to build the object. The processing logic may also render emphasis near the outline, such as a highlight, a bright color, an animation, etc. At block 935, the processing logic may determine whether the outline is full. A full outline may indicate that the player has placed a construction toy in the space occupied by the outline (i.e., in an instructed location). When the outline is full ("YES" at block 935), the processing logic may generate a reinforcement associated with the archetype A at block 940. For example, the reinforcement may include an indication of success, an icon, an animation, a sound, a haptic output (e.g., a vibration), or any other message or notification.

When the outline is not full ("NO" at block 935), the processing logic may wait for a predetermined amount of time at block 945. After waiting the predetermined amount of time, at block 950, the processing logic may determine whether the outline is full. When the outline is not full ("NO" at block 950), the processing logic may generate a next move. Generating the next move may include making the move for the player (e.g., direct prompting) by placing the construction toy in the outline. When the outline is full ("YES" at block 935), the processing logic may proceed to block 930.

Figure 10:
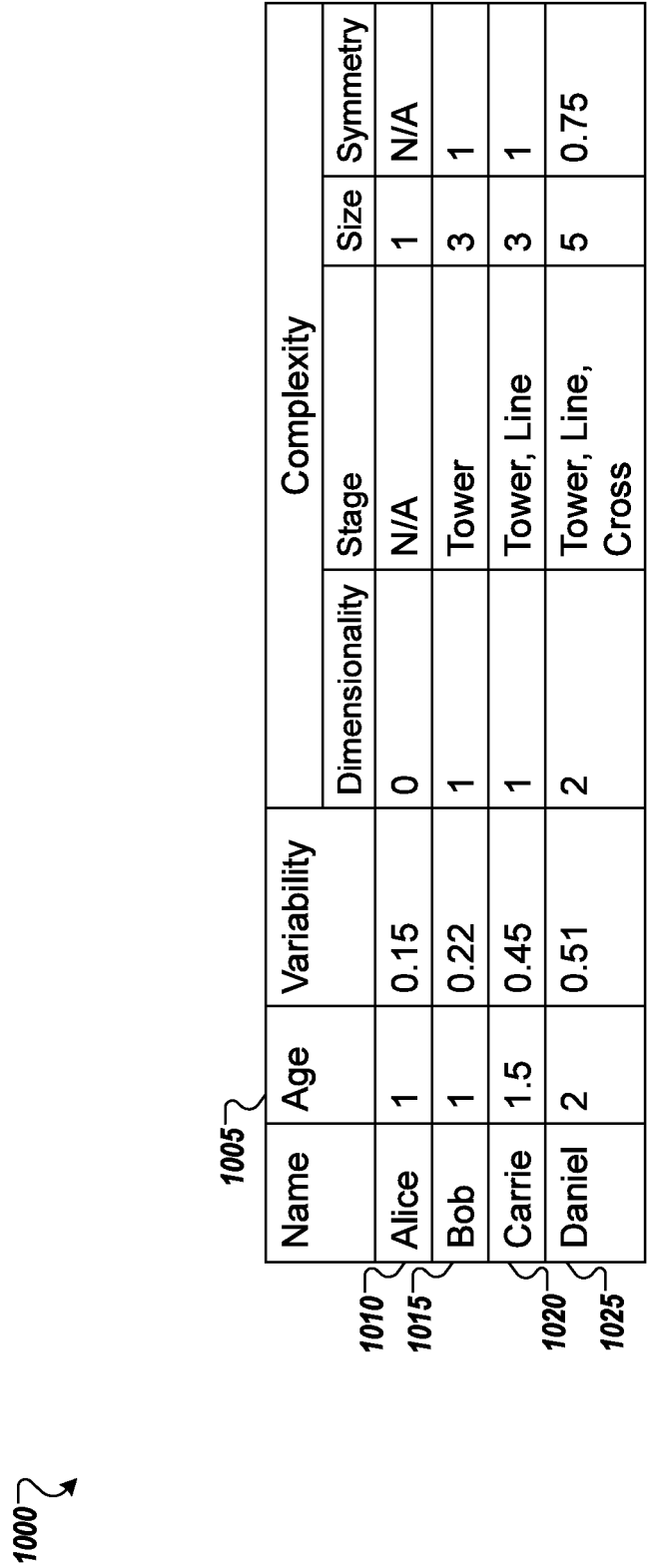
FIG. 10 illustrates an example play skill database that may include individual assessment data pertaining to one or more players.

FIG. 10 illustrates an example play skill database 1000 that may include individual assessment data pertaining to one or more players. The data in the play skill database 1000 may be indexed by any field. As illustrated, the play skill database 1000 is indexed by age. The play skill database 1000 may include one or more rows and columns. As illustrated, the columns include data labels 1005. The data labels 1005 may include name, age, variability, complexity (e.g., dimensionality, stage, size, symmetry), novelty, among other data labels. The play skill database 1000 may include one row per player. As illustrated, row 1010 include data associated with Alice, including an age of 1, a variability of 0.15, dimensionality of 0, stage N/A, size 1, and symmetry N/A. As illustrated, row 1015 include data associated with Bob, including an age of 1, a variability of 0.22, dimensionality of 1, stage tower, size 3, and symmetry 1. Similar data for Carrie and Daniel is illustrated in rows 1020 and 1025, respectively.

Figures 11A, 11B:
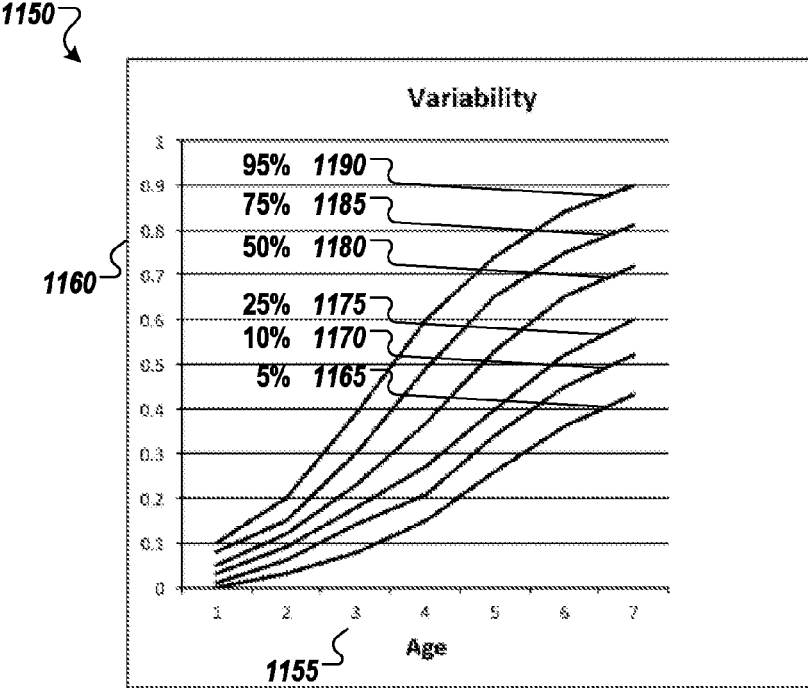
FIG. 11A illustrates an example aggregate complexity database that may include group assessment data.
FIG. 11B illustrates a graphical representation of variability in building construction toys as a function of age.

FIG. 11A illustrates an example aggregate complexity database 1100 that may include group assessment data that may have include aggregated data pertaining to multiple players. The aggregate complexity database 1100 may include rows 1105 and columns 1110. The aggregate complexity database 1100 may include aggregated data for a particular group of players. As illustrated, the aggregate complexity database 1100 include aggregated data for 2 year old players. The top row may include data labels. As illustrated, the data labels may include a count column that indicates a percentage of players (e.g., 2 year olds) that match the data in the other columns, dimensionality, stage, size, symmetry, etc. In an example, the lower 10% of 2 year olds built object with "1" dimensionality, where the stage was a "tower," the size was "3," and the symmetry was "1."

FIG. 11B illustrates a graphical representation of variability in building construction toys as a function of age. The x-axis 1155 may denote an age of the player. The y-axis 1160 may denote the variability in the player's actions. Curve 1165 represented the scores of the lower 5% of the sampled population, meaning a player at this level scores higher than 5% of the all sampled population. Similarly, curve 1170 represents 10%, curve 1175 represents 25%, curve 1180 represents 50%, curve 1185 represents 75%, and curve 1190 represents 95%.

Figure 12:
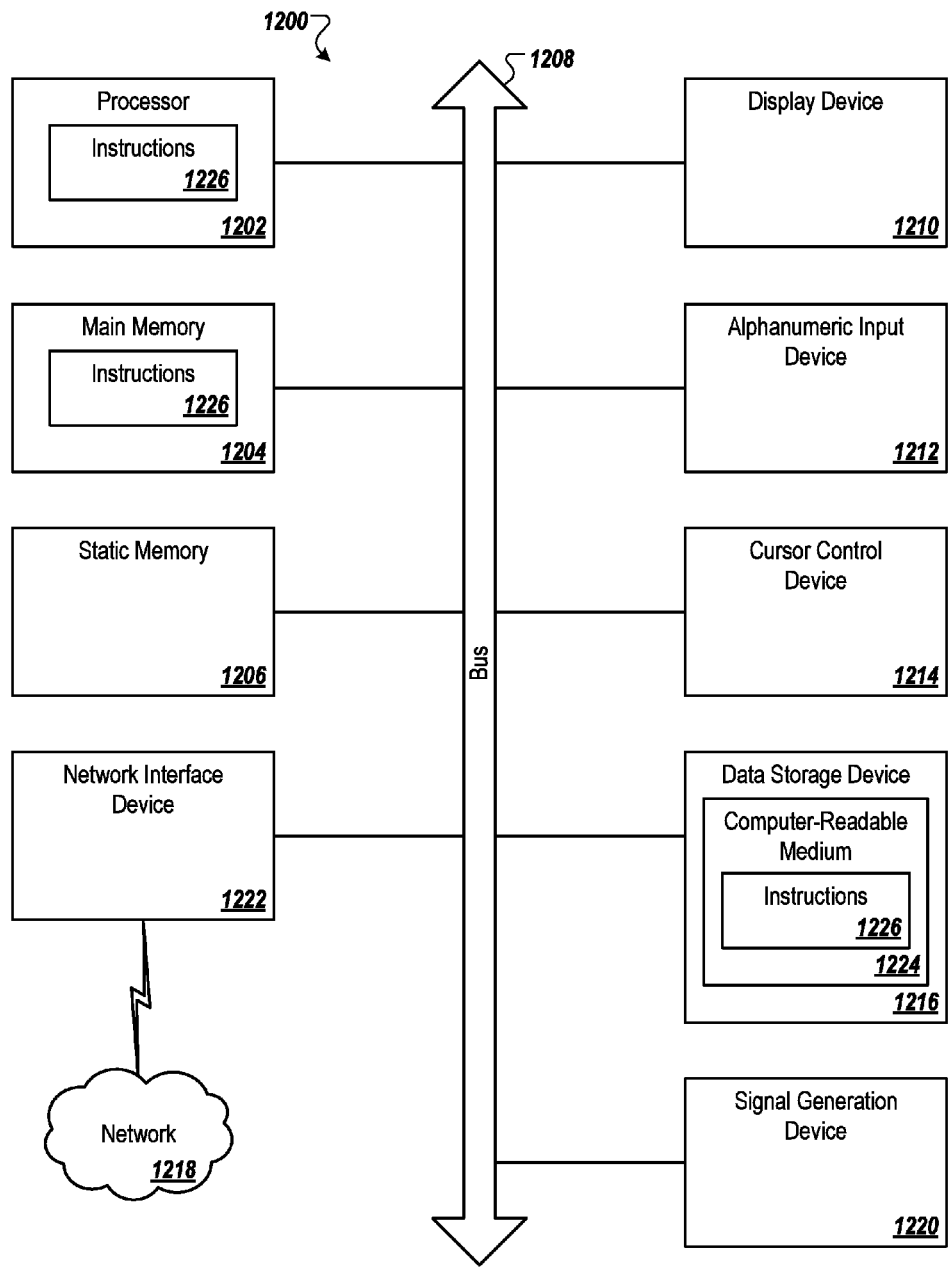
FIG. 12 illustrates a diagrammatic representation of a machine in the example form of a computing device within which a set of instructions, for causing the machine to perform any one or more of the methods discussed herein, may be executed.

FIG. 12 illustrates a diagrammatic representation of a machine in the example form of a computing device 1200 within which a set of instructions, for causing the machine to perform any one or more of the methods discussed herein, may be executed. The computing device 1200 may include a mobile phone, a smart phone, a netbook computer, a rackmount server, a router computer, a server computer, a personal computer, a mainframe computer, a laptop computer, a tablet computer, a desktop computer etc., within which a set of instructions, for causing the machine to perform any one or more of the methods discussed herein, may be executed. In alternative embodiments, the machine may be connected (e.g., networked) to other machines in a LAN, an intranet, an extranet, or the Internet. The machine may operate in the capacity of a server machine in client-server network environment. The machine may be a personal computer (PC), a set-top box (STB), a server, a network router, switch or bridge, or any machine capable of executing a set of instructions (sequential or otherwise) that specify actions to be taken by that machine. Further, while only a single machine is illustrated, the term "machine" may also include any collection of machines that individually or jointly execute a set (or multiple sets) of instructions to perform any one or more of the methods discussed herein.

The example computing device 1200 includes a processing device (e.g., a processor) 1202, a main memory 1204 (e.g., read-only memory (ROM), flash memory, dynamic random access memory (DRAM) such as synchronous DRAM (SDRAM)), a static memory 1206 (e.g., flash memory, static random access memory (SRAM)) and a data storage device 1216, which communicate with each other via a bus 1208.

Processing device 1202 represents one or more general-purpose processing devices such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1202 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computing device 1200 may further include a network interface device 1222 which may communicate with a network 1218. The computing device 1200 also may include a display device 1210 (e.g., a liquid crystal display (LCD) or a cathode ray tube (CRT)), an alphanumeric input device 1212 (e.g., a keyboard), a cursor control device 1214 (e.g., a mouse) and a signal generation device 1220 (e.g., a speaker). In one implementation, the display device 1210, the alphanumeric input device 1212, and the cursor control device 1214 may be combined into a single component or device (e.g., an LCD touch screen).

The data storage device 1216 may include a computer-readable storage medium 1224 on which is stored one or more sets of instructions 1226 embodying any one or more of the methods or functions described herein. The instructions 1226 may also reside, completely or at least partially, within the main memory 1204 and/or within the processing device 1202 during execution thereof by the computing device 1200, the main memory 1204 and the processing device 1202 also constituting computer-readable media. The instructions may further be transmitted or received over a network 1218 via the network interface device 1222.

While the computer-readable storage medium 1226 is shown in an example embodiment to be a single medium, the term "computer-readable storage medium" may include a single medium or multiple media (e.g., a centralized or distributed database and/or associated caches and servers) that store the one or more sets of instructions. The term "computer-readable storage medium" may also include any medium that is capable of storing, encoding or carrying a set of instructions for execution by the machine and that cause the machine to perform any one or more of the methods of the present disclosure. The term "computer-readable storage medium" may accordingly be taken to include, but not be limited to, solid-state memories, optical media and magnetic media.

Terms used herein and especially in the appended claims (e.g., bodies of the appended claims) are generally intended as "open" terms (e.g., the term "including" may be interpreted as "including, but not limited to," the term "having" may be interpreted as "having at least," the term "includes" may be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases may not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" may be interpreted to mean "at least one" or "one or more"); the same holds true for the use of definite articles used to introduce claim recitations.

In addition, even if a specific number of an introduced claim recitation is explicitly recited, those skilled in the art will recognize that such recitation may be interpreted to mean at least the recited number (e.g., the bare recitation of "two recitations," without other modifiers, means at least two recitations, or two or more recitations). Further, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the description, claims, or drawings, may be understood to contemplate the possibilities of including one of the terms, either of the terms, or both terms. For example, the phrase "A or B" may be understood to include the possibilities of "A" or "B" or "A and B."

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general purpose or special purpose computer. Combinations of the above may also be included within the scope of computer-readable media.

Computer-executable instructions may include, for example, instructions and data which cause a general purpose computer, special purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general purpose hardware), specific hardware implementations or a combination of software and specific hardware implementations are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it may be understood that the various changes, substitutions, and alterations may be made hereto without departing from the spirit and scope of the present disclosure.

The term "substantially" means within 5% or 10% of the value referred to or within manufacturing tolerances.

Various embodiments are disclosed. The various embodiments may be partially or completely combined to produce other embodiments.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Some portions are presented in terms of algorithms or symbolic representations of operations on data bits or binary digital signals stored within a computing system memory, such as a computer memory. These algorithmic descriptions or representations are examples of techniques used by those of ordinary skill in the data processing art to convey the substance of their work to others skilled in the art. An algorithm is a self-consistent sequence of operations or similar processing leading to a desired result. In this context, operations or processing involves physical manipulation of physical quantities. Typically, although not necessarily, such quantities may take the form of electrical or magnetic signals capable of being stored, transferred, combined, compared, or otherwise manipulated. It has proven convenient at times, principally for reasons of common usage, to refer to such signals as bits, data, values, elements, symbols, characters, terms, numbers, numerals, or the like. It should be understood, however, that all of these and similar terms are to be associated with appropriate physical quantities and are merely convenient labels. Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical, electronic, or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for-purposes of example rather than limitation, and does not preclude inclusion of such modifications, variations, and/or additions to the present subject matter as would be readily apparent to one of ordinary skill in the art.

What is claimed is:

1. A method, comprising:
acquiring individual assessment data that comprises behavior of a player of a construction toy, the construction toy includes at least one sensor to detect an activity of the player with the construction toy;
determining, by a processing device, a goal for the player based on the individual assessment data and a set of group assessment data;
providing a teaching based on the goal;
monitoring the activity of the player with the construction toy;
analyzing a construction state of the construction toy to determine that the player has met a construction toy milestone;
setting a play mode of the construction toy to a free play mode to permit the player to play with the construction toy with reduced monitoring during a free play period;
refraining from recording the activity of the player with the construction toy during the free play period;
determining that the free play period is over;
responsive to determining that the free play period is over, setting the play mode of the construction toy to a monitored mode;
prompting the player to perform an activity based on the goal in response to the play mode of the construction toy being set to the monitored mode; and
providing an electronic communication to the player in response to a determination that the player has completed the activity as detected by the sensor.

2. The method of claim 1, wherein providing the teaching based on the goal comprises:
selecting a construction model based on the goal;
instructing the player to build an object based on a construction model; and
outputting a second electronic communication to the player in response to a determination that the object has been built.

3. The method of claim 2, wherein the activity includes a request to build at least a portion of the object.

4. The method of claim 1, wherein prompting the player to perform the activity based on the goal comprises:
classifying the activity into an archetype group;
identifying a closest archetype to the activity in the archetype group;
setting the closest archetype as an object the player is to build;
identifying a missing substructure of the object;
generating an instruction for the player to place the construction toy at the missing substructure of the object; and
generating the electronic communication message in response to a determination that the construction toy has been placed at the missing substructure of the object.

5. The method of claim 4, wherein the construction toy is a digital representation of a physical construction toy, the method further comprising:
providing an electronic interface by which the player may interact with the construction toy; and
placing the construction toy at the missing substructure of the object within the electronic interface in response to a determination that the missing substructure of the object remains.

6. The method of claim 1, wherein the goal pertains to teaching the player to change a repetitive behavior, wherein the repetitive behavior is determined based on the individual assessment data.

7. The method of claim 1, wherein the electronic communication comprises one or more of: a text-based message, a sound, or a haptic output.

8. A system comprising:
a memory; and
a processor operatively coupled to the memory, the processor being configured to execute instructions to:
acquire individual assessment data that comprises behavior of a player of a construction toy, the construction toy includes at least one sensor to detect an activity of the player with the construction toy;
determine a goal for the player based on the individual assessment data and a set of group assessment data;
provide a teaching based on the goal;
monitor the activity of the player with the construction toy;
analyze a construction state of the construction toy to determine that the player has met a construction toy milestone;
setting a play mode of the construction toy to a free play mode to permit the player to play with the construction toy with reduced monitoring during a free play period;
refrain from recording the activity of the player with the construction toy during the free play period;
determine that the free play period is over;
responsive to determining that the free play period is over, set the play mode of the construction toy to a monitored mode;
prompt the player to perform an activity based on the goal in response to the play mode of the construction toy being set to the monitored mode; and
provide an electronic communication to the player in response to a determination that the player has completed the activity as detected by the sensor.

9. The system of claim 8, wherein when providing the teaching based on the goal, the processor is configured to:
select a construction model based on the goal;
instruct the player to build an object based on a construction model; and
output a second electronic communication to the player in response to a determination that the object has been built.

10. The system of claim 9, wherein the activity includes a request to build at least a portion of the object.

11. The system of claim 8, wherein when prompting the player to perform the activity based on the goal, the processor is configured to:
classify the activity into an archetype group;
identify a closest archetype to the activity in the archetype group;
set the closest archetype as an object the player is to build;
identify a missing substructure of the object;
generate an instruction for the player to place the construction toy at the missing substructure of the object; and
generate the electronic communication in response to a determination that the construction toy has been placed at the missing substructure of the object.

12. The system of claim 11, wherein the construction toy is a digital representation of a physical construction toy, the processor being further configured to:
- provide an electronic interface by which the player may interact with the construction toy; and
- place the construction toy at the missing substructure of the object within the electronic interface in response to a determination that the missing substructure of the object remains.

13. The system of claim 8, wherein the goal pertains to teaching the player to change a repetitive behavior, wherein the repetitive behavior is determined based on the individual assessment data.

14. A non-transitory computer readable medium having stored therein executable code that, when executed by a processor, cause the processor to perform operations comprising:
- acquiring individual assessment data that comprises behavior of a player of a construction toy, the construction toy includes at least one sensor to detect an activity of the player with the construction toy;
- determining a goal for the player based on the individual assessment data and a set of group assessment data;
- providing a teaching based on the goal;
- monitoring the activity of the player with the construction toy;
- analyzing a construction state of the construction toy to determine that the player has met a construction toy milestone;
- setting a play mode of the construction toy to a free play mode to permit the player to play with the construction toy with reduced monitoring during a free play period;
- refraining from recording the activity of the player with the construction toy during the free play period;
- determining that the free play period is over;
- responsive to determining that the free play period is over, setting the play mode of the construction toy to a monitored mode;
- prompting the player to perform an activity based on the goal in response to the play mode of the construction toy being set to the monitored mode; and
- providing an electronic communication to the player in response to a determination that the player has completed the activity as detected by the sensor.

15. The non-transitory computer readable medium of claim 14, wherein providing the teaching based on the goal comprises:
- selecting a construction model based on the goal;
- instructing the player to build an object based on a construction model; and
- outputting a second electronic communication to the player in response to a determination that the object has been built.

16. The non-transitory computer readable medium of claim 15, wherein the activity includes a request to build at least a portion of the object.

17. The non-transitory computer readable medium of claim 14, wherein prompting the player to perform the activity based on the goal comprises:
- classifying the activity into an archetype group;
- identifying a closest archetype to the activity in the archetype group;
- setting the closest archetype as an object the player is to build;
- identifying a missing substructure of the object;
- generating an instruction for the player to place the construction toy at the missing substructure of the object; and
- generating the electronic communication in response to a determination that the construction toy has been placed at the missing substructure of the object.

18. The non-transitory computer readable medium of claim 17, wherein the construction toy is a digital representation of a physical construction toy, the operations further comprising:
- providing an electronic interface by which the player may interact with the construction toy; and
- placing the construction toy at the missing substructure of the object within the electronic interface in response to a determination that the missing substructure of the object remains.

19. The non-transitory computer readable medium of claim 14, wherein the goal pertains to teaching the player to change a repetitive behavior, wherein the repetitive behavior is determined based on the individual assessment data.

20. The non-transitory computer readable medium of claim 14, wherein the first reinforcement message comprises one or more of: a text-based message, a sound, or a haptic output.

* * * * *